United States Patent [19]

Rennerfelt

[11] Patent Number: 5,013,325

[45] Date of Patent: May 7, 1991

[54] ARTIFICIAL LEG

[76] Inventor: Gustav Rennerfelt, Nilstorpsvägen 53, S-181 47 Lidingö, Sweden

[21] Appl. No.: 263,797

[22] PCT Filed: May 12, 1987

[86] PCT No.: PCT/SE87/00233

§ 371 Date: Oct. 26, 1988

§ 102(e) Date: Oct. 26, 1988

[87] PCT Pub. No.: WO87/06819

PCT Pub. Date: Nov. 19, 1987

[30] Foreign Application Priority Data

May 12, 1986 [SE] Sweden .............................. 8602143

[51] Int. Cl.5 .............................................. A61F 2/62
[52] U.S. Cl. ........................................ 623/38; 623/27
[58] Field of Search .............................. 623/27, 38, 39

[56] References Cited

U.S. PATENT DOCUMENTS

| 3,206,235 | 9/1965 | Albinson et al. | 623/38 X |
| 3,414,908 | 12/1968 | Waggott | 623/38 |
| 3,422,462 | 11/1969 | Finnieston | 623/38 |
| 3,538,516 | 11/1970 | Bailey | 623/38 |
| 3,659,294 | 5/1972 | Glabiszewski | 623/38 |
| 3,982,278 | 9/1976 | May | 623/47 X |
| 4,536,898 | 8/1985 | Palfuy | 623/27 |
| 4,608,054 | 8/1986 | Schröder | 623/39 |
| 4,676,800 | 6/1987 | Chen | 623/38 |
| 4,728,336 | 3/1988 | Cooper | 623/38 |

FOREIGN PATENT DOCUMENTS

| 2410998 | 7/1979 | France | 623/38 |
| 0535946 | 7/1977 | U.S.S.R. | 623/38 |
| 1026803 | 7/1983 | U.S.S.R. | 623/38 |
| 2089216 | 6/1982 | United Kingdom | 623/39 |

Primary Examiner—Randall L. Green
Assistant Examiner—David H. Willse
Attorney, Agent, or Firm—Witherspoon & Hargest

[57] ABSTRACT

A leg prosthesis with a tube (10), and adjusting head (11) arranged in the proximal end (4) of the tube. First means (16) allow adjustment of the angular attitude of the tube relative an imagined load line. Second means (12,13) allow translatory movement of the tube (10) relative the adjusting head (11). Fixing means fix the tube in a desired translated position relative the sleeve. The first and second means are both situated on the adjusting head at the proximal end of the tube, and both allow basic adjustment of the tube with the prosthesis in position of the wearer.

10 Claims, 5 Drawing Sheets

ARTIFICIAL LEG

The present invention relates to an artificial leg or leg prosthesis of the kind including a tube, an adjusting head arranged in the proximal end of the tube and intended for attaching the prosthesis to a sleeve mounted on the leg for adjusting the angular position of the tube relative an imagined load line.

A prior art leg prosthesis is illustrated in FIG. 1 and has a tube 1 which is upwardly articulately attached to a head 3 via a first joint 2, the head 3 in turn being attached to an outer sleeve 4, which is arranged on an inner sleeve 5, which is pushed over the stump 6 of the leg. Downwardly, at the distal end of the tube, there is a second articulate joint 7 attached to a foot 8. The chain-dotted line 9 denotes the socalled load line, i.e. an imaged line extending between the foot joint (represented by the joint 7) and the knee, the body weight ideally acting along this line.

An incorrect adjustment means that the wearer of the leg prosthesis loads the leg unnaturally, which results in that when the patient walks the movement pattern of the prosthesis will be unnatural, and also that where there is a knee joint, it and the leg muscles will be unnaturally loaded. In connection with the manufacture of the sleeve 4, the head 3 is moulded in plastics in the best possible position relative the load line 9. In the final walking test, an adjustment must usually be made, partly with the aid of the articulate joint 2 so that the joint 7 coincides with the load line 9, and partly with the joint 7 so that the foot is given the best attitude relative the ground plane. The structure can be linked to a tube with lockable universal joints at each end.

The disadvantage with this design principle is that the distal adjustment means, i.e. the joint 7, has a weight which gives an undesirable, distal loading moment on the stump left after amputation. A clear tendency in orthopedics is that the artificial foot is made as light as possible and that possible adjustment means are placed in the upper part of the prosthesis.

If the entire adjustment means is to be placed in the proximal or upper end of the prosthesis, and if it is to have the same adjustment facilities as in the structure described above, it must have both an angular adjustment facility such as the articulate joint 2 and a rectilinear translatory adjustment facility substantially in the horizontal plane.

There are structures where the final prosthesis tube is sustituted during trials by a temporary tube having at its upper end an adjusting instrument, e.g. a Hosmer instrument, which allows both angular and translational adjustment. After walking tests with the prosthesis and subsequent adjustment thereof, the entire prosthesis is placed in a fixture where the temporary tube and its adjustment instrument is replaced by the final prosthesis tube, which is moulded to the outer sleeve 4 with the aid of a thermosetting resin.

The advantage with this design principle (which is used more and more) is that the finished prosthesis will be light. However, the disadvantages are inter alia the time-consuming extra moulding of the tube, which usually requires a further fitting visit by the patient, and the relatively heavy adjusting instrument which loads the leg during the walking trial with a weight other than that of the final prosthesis. When the final prosthesis tube has been moulded in, no adjustment facility remains. This latter disadvantage is serious, since, particularly in amputations, the stump changes its shape due to the changes in swelling during the healing process. It is then often necessary not only to modify the inner sleeve 5, but is some times also desirable to make an extra adjustment of an angular and/or translatory nature.

Another known prosthesis uses the same method with an adjusting instrument and fixture aS described above, but provides the final prosthesis tube with an adjustment head allowing certain limited extra adjustment facilities. The disadvantages with this known prosthesis are also the required extra fitting visit by the patient, the heavy adjusting instrument, and the work in connection with placing the prosthesis in the fixture.

A still further prior art prosthesis uses a proximally mounted adjustment head comprising flat, mutually glidable plates. The upper surface of the upper plate has a bowl-shaped depression in which an element fixed to the sleeve is in complemental engagement. After the desired translatory and angular attitude positions have been adjusted for the prosthesis tube, the plates are fixed to each other with the aid of wood screws and the edges of the plates are cut off. No later adjustment facility for the prosthesis tube is available in this structure.

The above-mentioned structures are based on the tube skeleton principle. When the prosthesis is finally tried out and ready, it is clothed in an individual cosmetic casing of foamed plastics or rubber material.

Another more seldom used principle is the shell principle. Here a finished leg is built up from composite material. The prosthesis will be light but the method is time-consuming, since later adjustment facilities are lacking, as well as the feeling of the soft parts in a natural leg.

The present invention has the object of providing a leg prosthesis of the kind described in the introduction, which allows both basic adjustment of the tube adjusting angles and position relative the load line so that the longitudinal axis of the tube coincides with the load line, as well as later adjustment facilities, i.e. adjustment of the angular attitude and position relative the load line of the tube after the prosthesis has been in use for some time. All adjustments will be made at the proximal end of the tube and none at its distal end. There is no adjustment means for the tube at its distal end. The weight distribution of the prosthesis is thus improved.

The present invention also has the object of providing a leg prosthesis of the kind described in the introduction, which permits a basic adjustment of the angles and translatory positions of the prosthesis tube relative the load line without using the known adjusting instrument and fixture mentioned above. The basic adjustment is thus made directly on the final prosthesis tube and with the tube and its adjustment head applied to the sleeve. The patient thus wears the prosthesis during its trial and adjustment.

Another object of the invention is to provide a leg prosthesis which readily allows adjustment of the angles and translatory positions of the tube after some time in use.

A further object of the invention is to provide a leg prosthesis which in a preferred embodiment allows the adjustment of the tube angular position in two mutually perpendicular planes, which means that when an angular position has been adjusted in one plane, this position is retained, i.e. does not change, when a later adjustment of the angle in the other plane is carried out. The angular adjustment operations thus do not affect each other.

A preferred embodiment of the invention will now be described in detail below and with reference to the accompanying drawings, on which FIG. 1 is a schematic side view of a known leg prosthesis, FIG. 2 is a side view of the invention prosthesis in a single plane, FIG. 3 illustrates the inventive prosthesis in a sectional view, FIGS. 4, 5 and 6 illustrate a sleeve included in the prosthesis in axial section, plan from above and side view.

Figure 1:
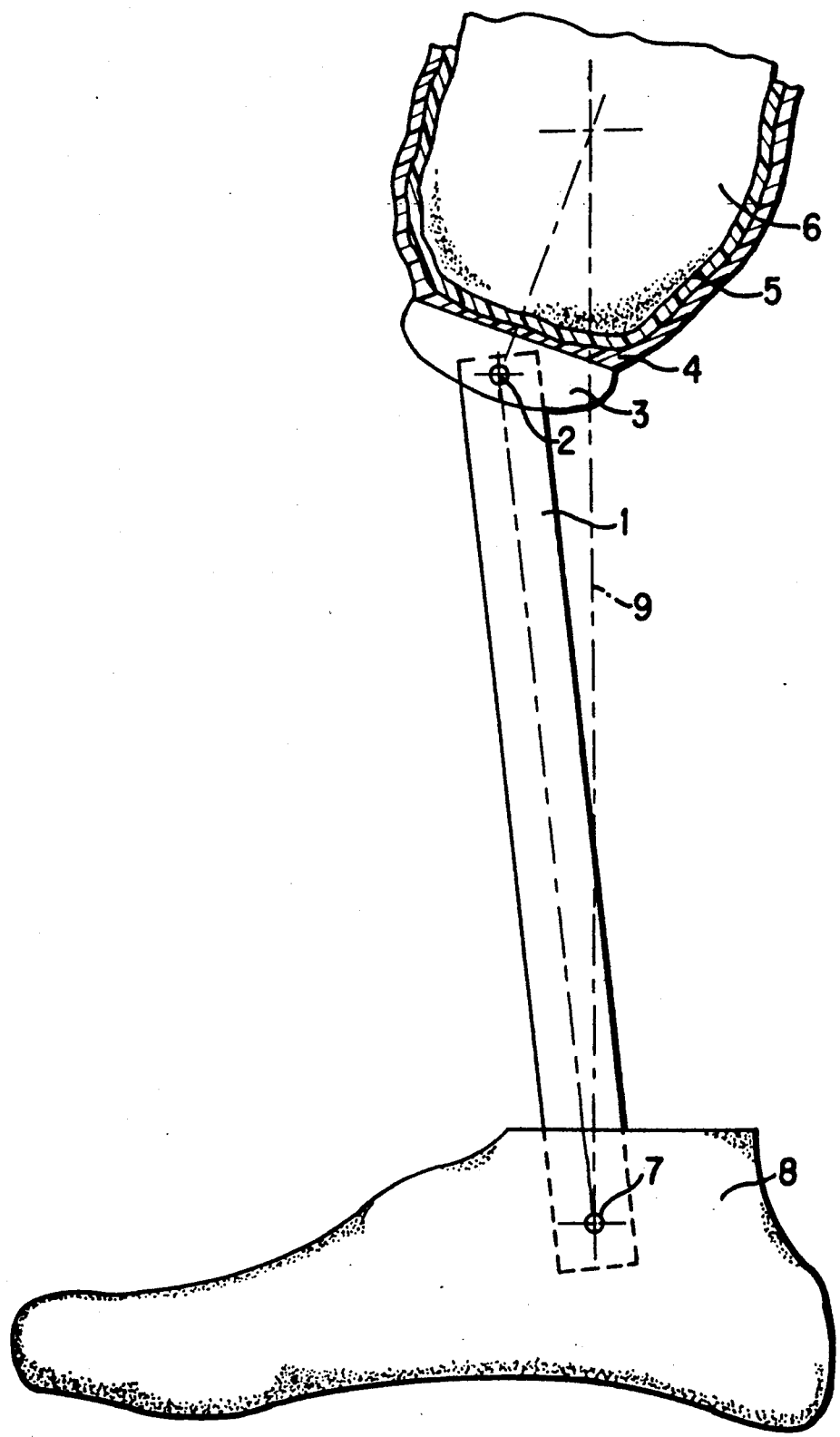
Figure 2:
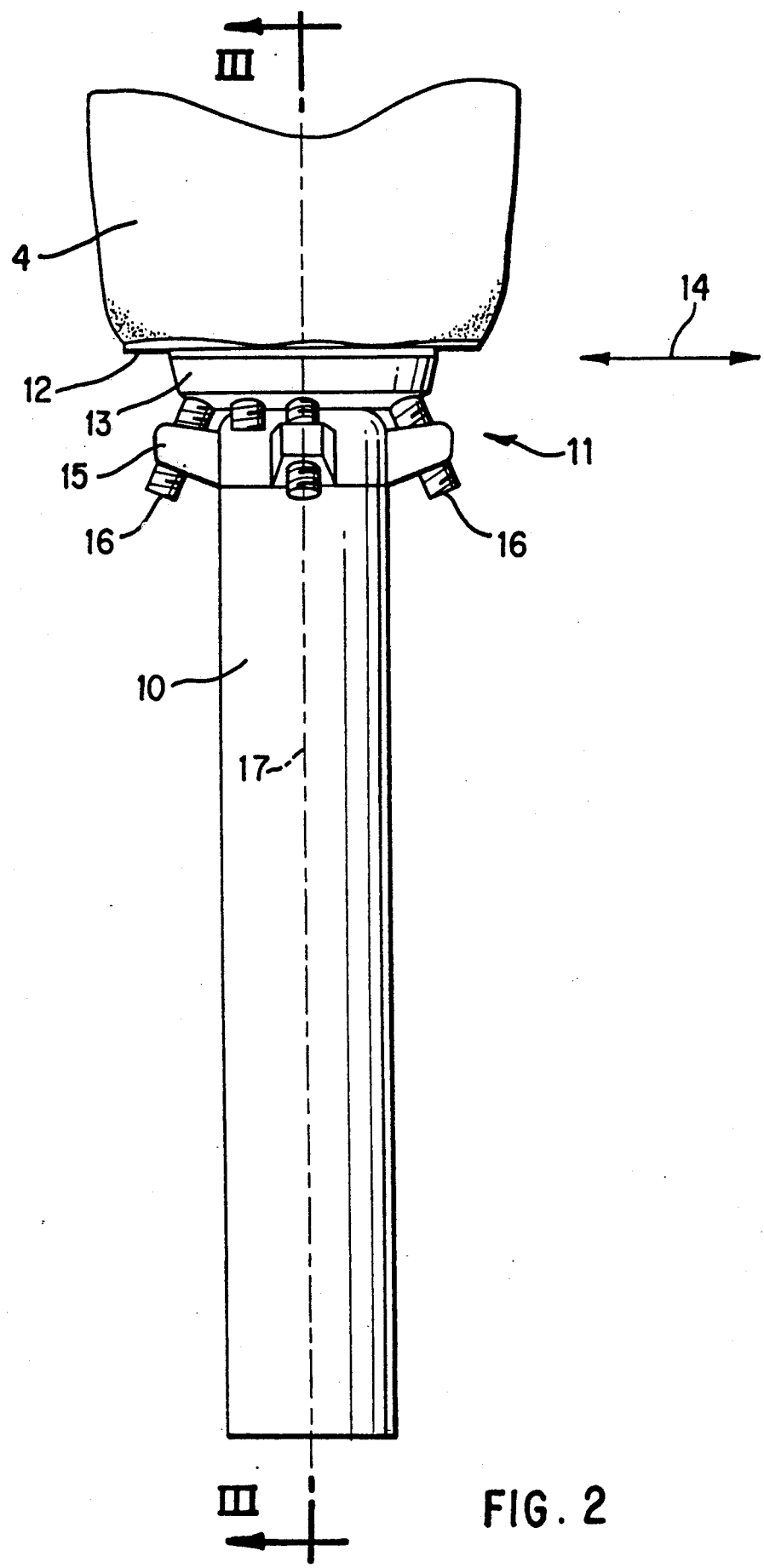
Figure 3:
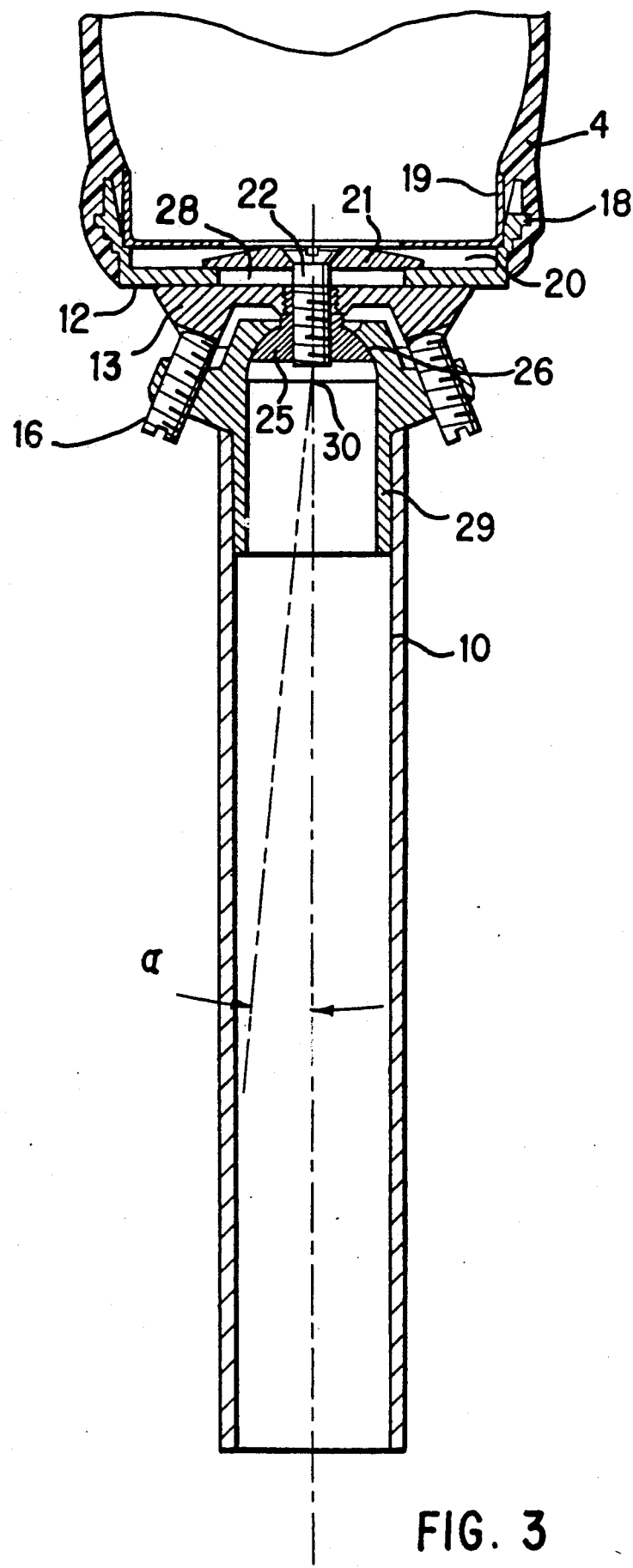

FIG. 2 is a side view of the leg prosthesis in accordance with the invention. The prosthesis includes a tube 10 with an adjusting head 11 arranged at the proximal end of the tube, this head being attached to the outer sleeve 4 of the leg. The head 11 includes an upper flat ring 12 and a lower flat carrying plate 13, the ring and plate being mutually relatively slidable, not only in the directions denoted by the arrows 14 but in all other directions in the interface between them. The head 11 also includes a sleeve 15, which is fastened to the proximal end of the tube 10 and has a plurality of adjusting screws 16, the function of which will be described in more detail below. The longitudinal axis of the tube 10 is denoted by the numeral 17. FIG. 3 is a section along the line III—III in FIG. 2, of the prosthesis illustrated in the latter FIGURE. As will be seen from FIG. 3, the ring 12 includes a flange 18, which is preferably integral with the ring and provided with a serrated exterior contour. The flange 18 is intended for moulding into the outer sleeve 4. On the inside of the flange there is a shoulder, on which rests a cover 19, for protection against the penetration of moulding composition into the space 20 formed under the cover. On the upper side of the ring 12 there is a holding-down plate 21 with a central hole. A screw 22, with its head resting on this plate is threaded into a hemispherical nut 25, which has its hemispherical surface 26 engaging slidingly against the complemental surface in the upper end portion 27 of the sleeve 15. On tightening the screw 22 this arrangement urges the plate 21 towards the lower carrying plate 13 such that these two bear against the ring 12. The holding-down plate 21 and carrying plate 13 are preferably circular, while the ring 12 has a central circular opening 28 allowing translatory movement to the screw shank. The dimensions of the ring 12, the circular opening 28 and the diameter of the holding-down plate 21 are such that the adjusting head 11, and thus also the tube 10, can be moved ±12.5 mm in all directions in the common plate between ring and carrying plate from the position illustrated in FIG. 3.

Figure 5:
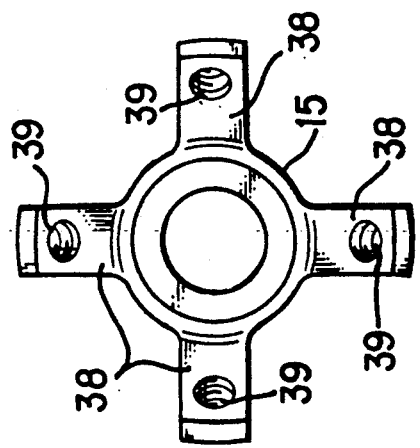
Figure 6:
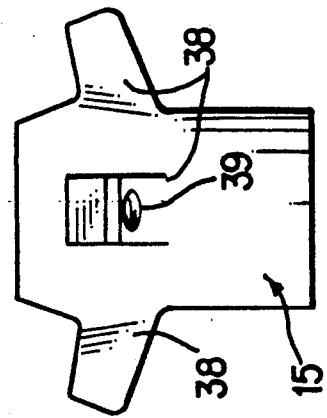
Figure 4:
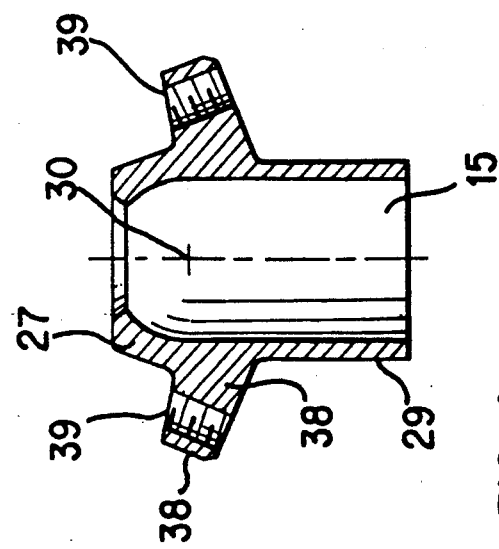
Figure 7:
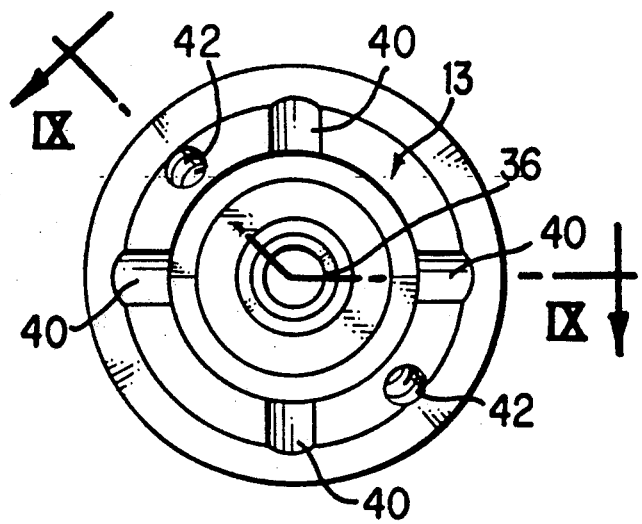
FIGS. 7, 8 and 9 illustrate a carrying plate included in the prosthesis in plan, section along the line IX—IX in FIG. 7 and side view.
Figure 8:
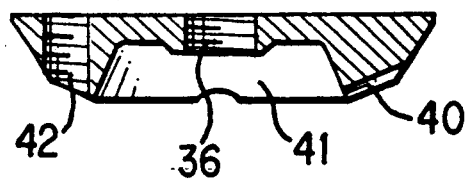
Figure 9:
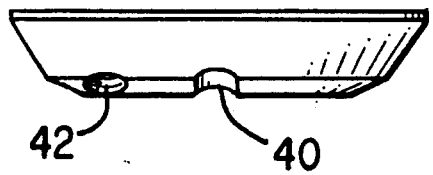
Figure 10:
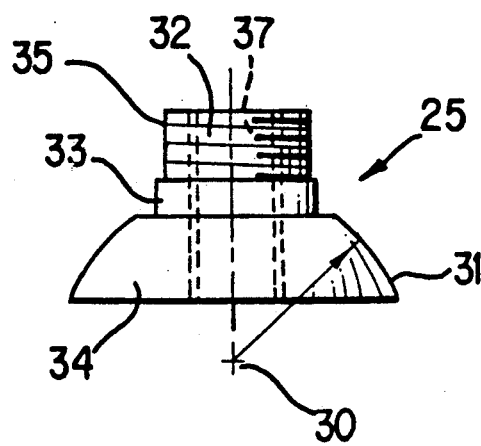
FIG. 10 is a side view of a hemispherical nut included in the prosthesis.

The angular adjustment of the longitudinal axis 17 of the tube 10 is perhaps easiest to understand if it is first imagined that the adjustment screws 16 are completely removed (which is a condition not normally present). The sleeve 15, illustrated in different views in FIGS. 4–6, has a throat 29, which is a sliding fit in the tube 10 and is locked by suitable, unillustrated means, e.g. pop rivets, to the tube 10. The internal wall of the upper end portion 27 of the sleeve 15 is rounded off, and in section has the form of a spherical sector with its centre indicated by the numeral 30. The spherical portion of the hemispherical nut 25 illustrated in FIG. 10 has it surface denoted by 31, and is complemental to the spherical surface 26 on the upper end portion 27, thus signifying that the surface 26 and 31 have the same radii and centre 30, which in its turn is situated in the throat 29 and coincident with the longitudinal axis 17 of the tube 10, as illustrated in FIG. 3. The hemispherical nut 25 comprises a stub shaft 32 with a shoulder 33 and a spherical segment 34. The stub shaft 32 has an external thread 35 which meshes with a threaded central opening 36 in the carrying plate 13 (see FIG. 8). The nut is also provided with a through internal thread 37 for the screw 22.

It will thus be clearly understood that the tube 10, retained by the sleeve, 15, can be set at different angular positions with the internal surface of the upper part 27 of the sleeve 15 sliding on the stationary spherical segment surface 31. The angular adjustment movements of the tube 10 can thus take place by rotation round an imagined rotational axis, which always passes through the centre 30. It will thus be clear that the tube can be pivoted universally around the centre 30. In the illustrated embodiment of the invention, the tube can be adjusted ±12° in all directions from the attitude illustrated in FIG. 3.

A description of how the angular position of the tube 10 can be adjusted and locked with the adjusting screws 16 in place will now be given. A plurality of arms 38 extend radially outwards from the wall of the sleeve 15 in the region of the bottom of the upper end portion 27. The arms form an angle of 68° with the longitudinal axis of the sleeve and slope upwards towards the level of the upper end portion 27. The arms, which are integral with the sleeve, are each provided with a threaded through hole 39 for receiving the adjusting screw 16.

These adjusting screws 16 are rounded at their forward ends and engage against grooves 40 made in the lower surface of the carrying plate 13. In its central portion the plate has a recess 41 for accommodating the end portion 27 of the sleeve 15. In the illustrated embodiment, the number of arms 38 and grooves 40 is preferably four and they are arranged with uniform distribution, i.e. 90°, about the centre of the threaded opening 36. In cross section, the grooves 40 have the form of circular or elliptical sectors, and the holes 39 are inclined relative the longitudinal axis of the sleeve, such that screwing in the left hand screw 16 in FIG. 3, accompanied by a corresponding loosening of the right hand screw, results in that the other two screws not illustrated in FIG. 3, since they are in a plane at right angles to the paper, slide on the surface of their respective grooves 40 with the centre of this pivoting movement situated at the centre 30. The movement is such that the forward ends of the two unillustrated screws glide on and follow the contour of the grooves 40. The angular adjustment of the tube is thus facilitated, since these two unillustrated screws do not need to be loosened when the screws 16 in FIG. 3 are rotated contra each other. It will be understood that apart from locking the set position, the screws also allow fine adjustment of the angular position of the tube. An important finesse with the invention is that the angular position of the tube can be adjusted even when the screw 22 has been finally tightened. It is thus possible, after the prosthesis has been in use for some time, to adjust its angular position without needing to remove it from the patient for the purpose of allowing access to the screw 22. That such later adjustment is possible will be understood from the fact that the hemispherical nut 25 is screwed down on the carrying plate 13 to form a single unit with it. Tightening the screw 22 fixes the translatory position of the carrying plate 13, since the ring 12 is firmly clamped between the holding-down plate 21 and the carrying plate 13. Tightening the screw 22 thus does not affect the possibility of angularly adjusting the tube with the aid of the adjusting screws 16.

By using four adjusting screws 16, four arms 38 and four grooves 40, all in uniform angular spacing, i.e. 90°, there is achieved the additional advantages that the angle, e.g. in FIG. 3, is set for the tube in one plane by complementally screwing the screws illustrated in FIG. 3, an adjustment of the tube angle in a plane at right angles to that of the paper can then be undertaken by complemental screwing of the unillustrated screws 16, without the previously set angle being altered. Should only three arms, screws and grooves at 120° to each other be used, a previously set angular position for one screw would be changed by an adjustment of the tube angle in another plane and the setting would need to be readjusted afterwards.

The carrying plate 13 also has two through threaded holes 42 for receiving two locking screws, unillustrated in FIGS. 2 and 3, with the aid of which the adjustment of the support plate 13 to the ring 12 can be temporarily fixed during trying-out the prosthesis until the correct translatory position has been obtained, these screws then being tightened finally. Any possible later angular adjustment by the screws 16 is not obstructed by this final fixation of the translatory position.

The basic setting of the prosthesis in accordance with the invention takes place in the following manner
(1) The prosthesis is put into position on the wearer, the tube is adjusted to a vertical position.
(2) The tube is translated so that it coincides with the load line.
(3) The unillustrated locking screws in the threaded holes 42 of the carrying plate 13 are tightened.
(4) The patient performs a walking test.
(5) The angular setting of the tube is adjusted with the adjusting screw 16, so that the tube does not move from side to side in the vertical plane during walking. Items (4) and (5) may be repeated.
(6) The head locking screw 22 is tightened.
(7) The whole adjusting head may be moulded-in while the patient waits. The adjusting screws 16 can also be covered with a thin and easily removable plastic layer.

The embodiment of the invention described above and illustrated on the drawings can be modified in may different ways, and varied within the scope of the invention concept.

I claim:

1. A leg prosthesis including an interface member, an adjusting head arranged at the proximal end of the interface member and intended for attaching the prosthesis to a first sleeve arranged on the leg stump, first means for adjusting the angular position of the interface member relative an imagined load line, second means for allowing a translatory movement of the interface member, and fixing means for fixing the interface member in a desired translatory position relative the first sleeve, said first and second means both being situated on the adjusting head at the proximal end of the interface member and both allowing basic adjustment of the interface member with the prosthesis in place on the patient, wherein said first means comprise a second sleeve fixed to the proximal end of the interface member, said second sleeve including a throat provided with a plurality of radially projecting arms arranged on the throat to form an angle with the longitudinal axis of the second sleeve, and a threaded through hole in the end portion of each arm for receiving an adjusting screw with a rounded end, said rounded end engaging against abutments of a lower surface of a support plate which is disposed below said first sleeve and forms a part of said second means.

2. A leg prosthesis in accordance with claim 1 wherein said second sleeve has a proximal end portion, the interior of which has the shape of a circle sector in cross section so as to form a surface shaped as a spherical segment.

3. A leg prosthesis in accordance with claim 2, wherein said support plate has a central, through hole for the fixing means and wherein said abutments take the form of radially directed grooves enabling the interface member to take up torque acting on its symmetrical axis.

4. A leg prosthesis as claimed in claim 3, wherein said grooves have a circular or elliptical sector as their cross sectional shape, the center of said sector being substantially in a horizontal plane crossing the center of the spherical surface of the second sleeve.

5. A leg prosthesis as claimed in claim 4, wherein said fixing means comprises a hemispherical nut and a fixing screw, said hemispherical nut including a stub shaft with an external thread and a spherical segment intended for engagement against the internal proximal portion of the second sleeve with the stub shaft projecting through said portion, said threaded stub shaft being intended for screwing into the through hole of the support plate, said spherical nut also having an internal thread intended for meshing with said fixing screw.

6. A leg prosthesis in accordance with claim 5, wherein the number of adjusting screws, arms on the second sleeve and grooves on the support plate is four, and wherein said items are arranged in mutual equally spaced angular relationship, i.e., 90° from each other.

7. A leg prosthesis in accordance with claim 6, wherein said second means include said support plate with a holding-down plate arranged above it, and a ring which is preferably circular and arranged between said support plate and the holding-down plate, the internal diameter of the ring being less than the extension of the holding-down plate, said fixing means being adapted for locking the ring between the holding-down plate and support plate and for fixing the structure formed by the holding-down plate, support plate and ring on the second sleeve, said second sleeve being mounted on the proximal end of the interface member, the ring having a projecting flange directed obliquely upwardly for fixing in the lower portion of the first sleeve.

8. A leg prosthesis in accordance with claim 7, wherein said fixing screw has a head and shank, said head engaging against the holding-down plate and said shank extending through a circular opening of said ring and into the internal thread of the spherical nut such that when the joint formed by the screw and the hemispherical nut is loosely tightened, the holding-down plate and support plate and thus also the interface member may carry out a translatory movement in an optional direction along the plane between the support plate and ring to an extent determined by the mutual dimensions between the holding-down plate and the internal diameter of the ring.

9. A leg prosthesis in accordance with claim 8, wherein a shoulder is provided on the inside of said flange of said ring and wherein a protective cover is arranged on the shoulder for protecting underlying details when the ring is moulded into the first sleeve.

10. A leg prosthesis in accordance with claim 9, wherein said fixing means further includes locking screws meshing in threads provided in the support plate, said locking screws being adapted to engage the ring.

* * * * *